(12) United States Patent
Huang et al.

(10) Patent No.: US 11,202,854 B2
(45) Date of Patent: Dec. 21, 2021

(54) DISINTEGRIN VARIANTS AND USES THEREOF

(71) Applicants: National Taiwan University, Taipei (TW); NATIONAL CHENG KUNG UNIVERSITY, Tainan (TW); DCB-USA LLC, Wilmington, DE (US)

(72) Inventors: Tur-Fu Huang, Taipei (TW); Yu-Ju Kuo, Taipei (TW); Woei-Jer Chuang, Tainan (TW)

(73) Assignees: NATIONAL TAIWAN UNIVERSITY, Taipei (TW); NATIONAL CHENG KUNG UNIVERSITY, Tainan (TW); DCB-USA LLC, Wilmington, DE (US)

( * ) Notice: Subject to any disclaimer, the term of this patent is extended or adjusted under 35 U.S.C. 154(b) by 191 days.

(21) Appl. No.: 16/636,908

(22) PCT Filed: Aug. 9, 2017

(86) PCT No.: PCT/US2017/046086
§ 371 (c)(1),
(2) Date: Feb. 6, 2020

(87) PCT Pub. No.: WO2019/032105
PCT Pub. Date: Feb. 14, 2019

(65) Prior Publication Data
US 2020/0164114 A1      May 28, 2020

(51) Int. Cl.
| | |
|---|---|
| *A61L 31/10* | (2006.01) |
| *A61K 47/60* | (2017.01) |
| *C07K 14/46* | (2006.01) |
| *A61K 38/00* | (2006.01) |
| *A61K 45/06* | (2006.01) |

(52) U.S. Cl.
CPC .............. *A61L 31/10* (2013.01); *A61K 47/60* (2017.08); *C07K 14/46* (2013.01); *A61K 38/00* (2013.01); *A61K 45/06* (2013.01); *A61L 2420/06* (2013.01)

(58) Field of Classification Search
CPC ..... A61L 2420/06; A61L 31/10; A61K 45/06; A61K 38/00; A61K 47/60; C07K 14/46
See application file for complete search history.

(56) References Cited

PUBLICATIONS

Inn-Ho Tsai, Ing-Ming Wang & Yi-Hsuan Lee, Characterization of a cDNA Encoding the Precursor of Platelet Aggregation Inhibitor and Metalloproteinase From Trimeresurus mucrosquamatus Venom, 1200 Biochim Biophys Acta 337 (Year: 1994).*
Francis Markland, Snake Venoms and the Hemostatic System, 36 Toxicon 1749 (Year: 1998).*
Paula Juarez, et al, Evolution of Snake Venom Disintegrins by Positive Darwinian Selection, 25 Mol. Biol. Evol. 2391 (Year: 2008).*

* cited by examiner

*Primary Examiner* — Sean M Basquill

(57) ABSTRACT

Disclosed herein are disintegrin variants, and methods for suppressing or inhibiting platelet aggregation in a subject in need thereof. The method includes administering to the subject in need thereof an effective amount of the present disintegrin variant to alleviate or ameliorate symptoms associated with diseases, disorders, and/or conditions resulted from platelet aggregation. According to preferred embodiments, the present disintegrin variant is applied as a coating on an implantable device, such as a stent or a catheter.

13 Claims, 3 Drawing Sheets
Specification includes a Sequence Listing.

DISINTEGRIN VARIANTS AND USES THEREOF

This application is a national stage filing under 35 U.S.C. 371 of International Application PCT/US2017/046086, filed Aug. 9, 2017, the content of which is hereby incorporated by reference herein.

BACKGROUND OF THE INVENTION

1. Field of the Invention

The present disclosure in general relates to novel disintegrin variants and their uses for suppressing platelet aggregation and platelets activation in a subject.

2. Description of Related Art

Platelets are involved in many physiologic and pathological processes such as atherothrombosis, stem cell trafficking, tumor metastasis, and arthritis. Platelet activation at sites of an intact inflamed endothelium contributes to vascular inflammation and vascular wall remodeling. Platelets interact with the vascular endothelium and link the processes of inflammation, thrombosis, and atherogenesis, which is mediated through the interactions between platelets and endothelial cells/leukocytes. Platelets can induce a variety of inflammatory responses in monocytes, neutrophils (PMN), endothelial cells, or endothelial progenitor cells (EPCs), resulting in key inflammatory processes, such as adhesion, chemotaxis, migration, thrombosis, or even monocytic cell differentiation to macrophages or foam cells.

Platelet activation plays an important role in the process of inflammation and the initiation of atherosclerosis. Many cardiovascular diseases (CVDs), including the initiation of atherothrombosis, are linked to the abnormal and excessive activation of platelets, or platelet hyperactivity, which is considered an independent risk factor for CVDs. Acetylsalicylic acid (aspirin) was the first antiplatelet agent identified, which irreversibly inhibits the cyclooxygenase 1 (COX1) enzyme in the arachidonic acid pathway through acetylation of the COX1 active site. Long-term aspirin therapy reduces the risk of subsequent myocardial infarction, stroke or vascular death among intermediate to high-risk patients with atherothrombotic disease by about 20%-25% (Patrono et al., 2004 Chest 126, 234S-264S). However, bleeding risk is a substantial limitation of antiplatelet therapy. Though recent novel antiplatelet agents, including clopidogrel and ticagrelor, provide potent antiplatelet effect on CVD therapy, bleeding remained an important clinical issue. Scientists are still working on the balance between bleeding and efficacy for a safe antiplatelet agent.

In view of the above, there exists in the related art a need of an agent that suppresses or inhibits the aggregation and/or activation of platelets without the bleeding risk concern, which is potential candidate for the development of a medicament for treating diseases, disorders, and/or conditions resulted from platelet aggregation.

SUMMARY

The following presents a simplified summary of the disclosure in order to provide a basic understanding to the reader. This summary is not an extensive overview of the disclosure and it does not identify key/critical elements of the present invention or to delineate the scope of the present invention. Its sole purpose is to present some concepts disclosed herein in a simplified form as a prelude to the more detailed description that is presented later.

In general, the present disclosure relates to the unexpected discovery of novel disintegrin variants that suppress platelet aggregation, platelet activation, and thrombus formation. Thus, these novel disintegrin variants are potential candidates for the development of medicaments for treating diseases and/or conditions resulted from platelet aggregation.

Accordingly, the first aspect of the present disclosure aims at providing a disintegrin variant that suppresses or inhibits platelet aggregation. The disintegrin variant comprises in its structure:

(a) a linker having the amino acid sequence of SEQ ID Nos. 1, 4, 7, 8, or 9;
(b) a RGD loop having the amino acid sequence of SEQ ID Nos. 11-20, 24 or 25; and
(c) a C-terminus having the amino acid sequence of SEQ ID Nos. 3, 6, 21, 22, or 23.

Examples of disintegrin of the present disclosure include, but are not limited to, albolabrin, applagin, basilicin, batroxostatin, bitistatin, cereberin, cerastin, crotatroxin, durissin, elegantin, eristicophin, flavoridin, flavostatin, halysin, halystatin, jararacin, jarastatin, kistrin, lachesin, lutosin, molossin, rhodostomin, salmosin, saxatilin, tergeminin, trimestatin, trimucrin, trimutase, ussuristatin, and viridian.

According to some preferred embodiments, the present disintegrin variant derives from trimucrin. According to other embodiments, the present disintegrin variant derives from rhodostomin.

In some embodiments, the disintegrin variant comprises, (a) the linker of SEQ ID No: 1;

(b) the RGD loop of any of SEQ ID Nos: 10-20; and (c) the C-terminus of any of SEQ ID Nos: 3, 21, 22, or 23.

In one preferred embodiment, the disintegrin variant comprises, the linker of SEQ ID No: 1, the RGD loop of SEQ ID No: 14, and the C-terminus of SEQ ID No. 21.

In further embodiments, the disintegrin variant comprises, (a) the linker of SEQ ID No: 7;

(b) the RGD loop of SEQ ID Nos: 13 or 18; and (c) the C-terminus of any of SEQ ID Nos: 3, 21, or 22.

In still further embodiments, the disintegrin variant comprises, the linker of SEQ ID No: 8; the RGD loop of SEQ ID No: 14; and the C-terminus of SEQ ID No: 21.

In still further embodiments, the disintegrin variant comprises, (a) the linker of SEQ ID No: 9;

(b) the RGD loop of SEQ ID Nos: 14 or 20; and (c) the C-terminus of any of SEQ ID Nos: 3, 21, or 22.

In other embodiments, the disintegrin variant comprises, the linker of SEQ ID No: 4; the RGD loop of SEQ ID No: 24 or 25; and the C-terminus of SEQ ID No: 6.

According to optional embodiments of the present disclosure, the disintegrin variant further comprises a polyethylene glycol (PEG) chain having 2-20 repeats of ethylene glycol (EG) units linked to the N-terminus of the disintegrin variant.

Accordingly, the second aspect of the present disclosure aims at providing a pharmaceutical composition for treating diseases and/or conditions resulted from platelet aggregation. The pharmaceutical composition comprises an effective amount of any of the disintegrin variant described above, and a pharmaceutically acceptable carrier.

According to preferred embodiments of the present disclosure, the disintegrin variant comprises in its structure, the linker of SEQ ID No: 1; the RGD loop of SEQ ID Nos: 14; and the C-terminus of SEQ ID No: 21.

According to optional embodiments, the disintegrin variant further comprises a polyethylene glycol (PEG) chain having 2-20 repeats of ethylene glycol (EG) units linked to the N-terminus of the disintegrin variant.

According to embodiments of the present disclosure, the disease and/or condition resulting from platelet aggregation is a thrombotic disorder, which may be selected from the group consisting of, abrupt vessel closure following angioplasty or stent placement, atherothrombosis, acute thrombotic stroke, myocardial infarction, thrombosis resulted from periphery vascular surgery, unstable angina, and venous thrombosis.

According to preferred embodiment of the present disclosure, the thrombotic disorder is atherothrombosis.

According to optional embodiments of the present disclosure, the pharmaceutical composition further comprises an anti-coagulant, which may be selected from the group consisting of, abciximab, apixaban, aspirin, clopidogrel, dipyridamole, edoxaban, eptifibatide, rivaroxaban, tirofiban, ticlopidine, warfarin, and vitamin K.

According to preferred embodiments, the disintegrin variant is applied as a coating on the surface of an implantable device, which includes and is not limited to, a stent and a catheter. Optionally, the disintegrin variant and the anti-coagulant are respectively applied as coatings on the surface of the implantable device.

The third aspect of the present disclosure aims at providing a method of treating a subject having or suspected of having a disease and/or a condition resulting from platelet aggregation. The method comprises administering to the subject the present pharmaceutical composition to alleviate or ameliorate the symptoms associated with the disease and/or condition resulting from platelet aggregation.

According to embodiments of the present disclosure, the disintegrin variant is administered to the subject in the amount of 0.01-100 mg/Kg. Preferably, the disintegrin variant is administered to the subject in the amount of 0.1-50 mg/Kg.

According to embodiments of the present disclosure, the disease and/or condition resulting from platelet aggregation is a thrombotic disorder, which may be selected from the group consisting of, abrupt vessel closure following angioplasty or stent placement, atherothrombosis, acute thrombotic stroke, myocardial infarction, thrombosis resulted from periphery vascular surgery, unstable angina, and venous thrombosis.

According to preferred embodiment of the present disclosure, the thrombotic disorder is atherothrombosis.

According to embodiments of the present disclosure, the method further comprises administering to the subject an anti-coagulant, which may be selected from the group consisting of, abciximab, apixaban, aspirin, clopidogrel, dipyridamole, edoxaban, eptifibatide, rivaroxaban, tirofiban, ticlopidine, warfarin, and vitamin K.

According to preferred embodiments of the present disclosure, the present disintegrin variant is applied as a coating on the surface of an implantable device, which includes and is not limited to, a stent and a catheter. Optionally, the disintegrin variant and the anti-coagulant are respectively applied as coatings on the surface of the implantable device.

Accordance to embodiments of the present disclosure, the subject is human.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in colors. Copies of this patent or patent application publication with color drawing(s) will be provided by the Office upon request and payment of the necessary fee.

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DESCRIPTION

Figure 1A:
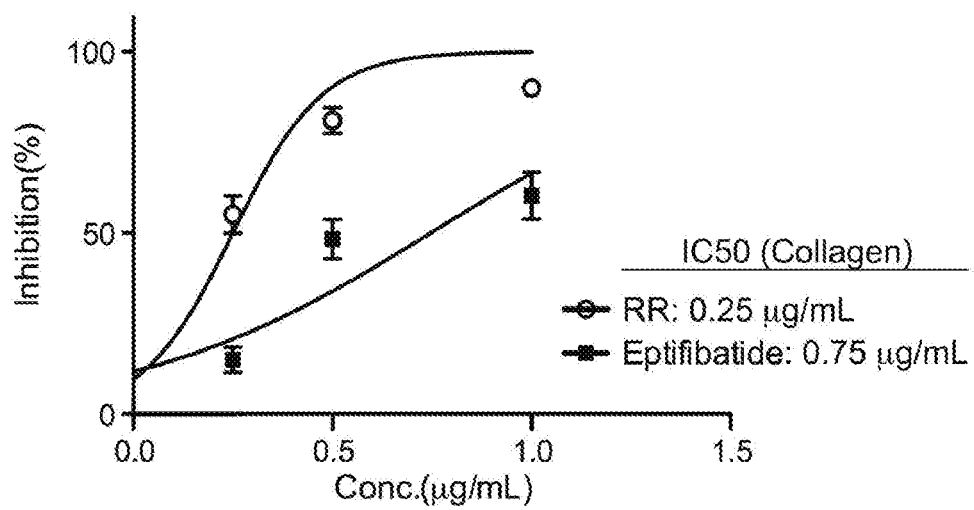
FIGS. 1A to 1C depicts the in vitro (A) and ex vivo (B-C) aggregation response of collagen-induced platelet aggregation treated with saline (control), trimucrin T/KRRR mutant (RR) or Ept (mean±s.e.m, error bars, n=8, ***P<0.001 compared with control group by Dunnett's test) in accordance with one embodiment of this invention.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

Throughout the present disclosure, the positions of any specified amino acid residues within a peptide are numbered starting from the N terminus of the peptide. When amino acids are not designated as either D- or L-amino acids, the amino acid is is either L-amino acid or could be either D- or L-amino acid, unless the context requires a particular isomer. The terms "D-amino acid" and "L-amino acid" are used to refer to absolute configuration of the amino acid, rather than a particular direction of rotation of plane-polarized light. The usage herein is consistent with standard usage by those skilled in the related art. Amino acids are designated herein using standard 1-letter code, e.g., as designated in Standard ST.25 in the Handbook On Industrial Property Information and Documentation.

As discussed herein, minor variations in the amino acid sequences of proteins/peptides are contemplated as being encompassed by the presently disclosed and claimed inventive concept(s), providing that the variations in the amino acid sequence is unrelated to its physiological activity. For example, certain amino acids can be changed and/or deleted without affecting the physiological activity of the peptide in this study (i.e., its ability to treat diseases and/or conditions resulting from platelet aggregation). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that a replacement of a leucine with an isoleucine or valine, an aspartate with a glutamate, a threonine with a serine, or a similar replacement of an amino acid with a structurally related amino acid will not have a major effect on the binding or properties of the resulting molecule. Whether an amino acid change results in a functional peptide can readily be determined by assaying the specific activity of the peptide derivative.

The term "polypeptide" and "protein" may be used interchangeably to refer to proteins produced by naturally occurring and non-recombinant cells, by genetically engineering or recombinant cells, or by chemical synthesis, and comprise molecules having substitution, deletion, and/or insertion of one or more amino acids of the native sequence. In accordance with embodiments of the present disclosure, the disintegrin variant are polypeptides or proteins encompass modified trimucrin and modified rhodostomin or fragments thereof that inhibit integrin αIIbβ3 activity.

The term "disintegrin" refers to a class of proteins purified from snake venoms, which contain in its structure at least, a linker region, an arginine-glycine-aspartic acid (RGD) motif located at the tip of a flexible loop of the integrin-binding domain, and a C-terminus. All disintegrins purified from snake venom may selectively bind to fibrinogen receptor, such as αIIbβ3 integrin, the binding of which results in the inhibition of fibrinogen-dependent platelet aggregation and other biological activities mediated by fibrinogen receptor. Disintegrins thus block fibrinogen-dependent functions and act as platelet aggregation inhibitors.

The term "disintegrin variant" refers to a functionally active protein, or a polypeptide or any derivatives thereof that comprises an amino acid sequence modified or mutated from a wild-type disintegrin such as rhodostomin (Rho) or trimucrin (TMV-7). According to embodiments of the present disclosure, a functionally active disintegrin variant can specifically bind to and inhibit integrin αIIbβ3 activity. The disintegrin variant of the present disclosure can be constructed by any method known in the related art, for example, site-directed mutagenesis or polymerase chain reaction. Variants may include insertions, additions, deletions, or substitutions compared with the subject peptides. Variants of polypeptide sequences include biologically active polymorphic variants.

In some embodiments of the present disclosure, the disintegrin variant comprises a modified trimucrin (TMV-7) protein that contains at least one amino acid substitution, insertion, or deletion compared with the naturally occurring TMV-7 (or the wild type TMV-7). In other embodiments of the present disclosure, the disintegrin variant comprises a modified rhodostomin (Rho) protein that contains at least one amino acid substitution, insertion, or deletion compared with the naturally occurring Rho (or the wild type Rho).

The term "a linker region" refers to the region of a disintegrin located immediately N-terminal to the RGD loop. For example, the linker region of TMV-7 comprises the amino acid sequence of SEQ ID No: 1 ($^{41}$KKKRT), whereas the linker region of Rho comprises the amino acid sequence of SEQ ID No: 4 ($^{39}$SRAGK). According to preferred embodiments of the present disclosure, the disintegrin variant comprises a mutant linker region, which comprises at least one mutation at position 1 to 5 of the amino acid sequence of SEQ ID No: 1 ($^{41}$KKKRT). Preferably, the disintegrin variant comprises a mutant linker that comprises the amino acid sequence selected from the group consisting of SEQ ID Nos: 7, 8, or 9. Alternatively, instead of having a mutant linker, the disintegrin variant of the present disclosure comprises the naturally occurring linker region of TMV-7 or Rho.

The term "RGD loop" refers to the RGD motif of a disintegrin. For example, the RGD loop of TMV-7 comprises the amino acid sequence of SEQ ID No: 2 ($^{50}$ARGDNP), whereas the RGD loop of Rho comprises the amino acid sequence of SEQ ID No: 5 ($^{48}$PRGDMP). According to some embodiments of the present disclosure, the disintegrin variant comprises a mutant RGD loop of TMV-7, which comprises at least one mutation at position 1 to 6 of the amino acid sequence of SEQ ID No: 2 ($^{50}$ARGDNP); more preferably, the disintegrin variant comprises the amino acid sequence selected from the group consisting of SEQ ID Nos: 11, 12, 13, 14, 15, 16, 17, 18, 19, and 20.

According to other embodiments of the present disclosure, the disintegrin variant comprises a mutant RGD loop of Rho, which comprises at least one mutation at position 1 to 6 of the amino acid sequence of SEQ ID No: 5 ($^{4}$PRGDMP), more preferably, the disintegrin variant comprises the amino acid sequence of SEQ ID No: 24 or 25.

The term "C-terminus" refers to the amino acid sequence of the C-terminus of a disintegrin. For example, the C-terminus of TMV-7 comprises the amino acid sequence of SEQ ID No: 3 ($^{67}$PRNGLYG), whereas the C-terminus of Rho comprises the amino acid sequence of SEQ ID No: 6 ($^{65}$PRYH). According to some embodiments of the present disclosure, the disintegrin variant comprises a mutant C-terminus of TMV-7, which comprises at least one mutation at position 1 to 7 of the amino acid sequence of SEQ ID No: 3 ($^{67}$PRNGLYG); more preferably, the disintegrin variant comprises the amino acid sequence selected from the group consisting of SEQ ID Nos: 6, 21, 22 and 23. Alternatively, instead of having a mutant C-terminus, the disintegrin variant comprises a naturally occurring C-terminus of TMV-7 (i.e., SEQ ID No: 3) or Rho (i.e., SEQ ID NO: 6).

According to preferred embodiments of the present disclosure, the disintegrin variant of the present disclosure comprises a mutant RGD. Additionally or optionally, the present disintegrin variant further comprises at least one of a mutant linker and a mutant C-terminus of a disintegrin.

The term "$IC_{50}$" refers to the concentration of a disintegrin or its variant that is required to inhibit a biological process by 50%, such as the platelet aggregation or cell adhesive activity.

The term "treatment" and "treating" are interchangeably used herein, and are intended to mean obtaining a desired pharmacological and/or physiologic effect, e.g., delaying or inhibiting platelet aggregation and/or platelet activation. The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., a cancer or heart failure) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "administered", "administering" or "administration" are used interchangeably herein to refer a mode of delivery, including, without limitation, intravenously, intramuscularly, intraperitoneally, intraarterially, intracranially, or to subcutaneously administering an agent (e.g., a compound or a composition) of the present invention. In some embodiments, the disintegrin variant of the present disclosure are formulated into powders for mixed with suitable carrier (e.g., buffer solution) before use, such as intravenous injection. In other embodiments, the disintegrin variant of the present disclosure is directly applied or coated onto an angioplasty stent (e.g., a coronary stent or a vascular stent) or a stent graft for use in a vascular surgical procedure.

The term "an effective amount" as used herein refers to an amount effective, at dosages, and for periods of time necessary, to achieve the desired result with respect to the treatment of a disease resulted from platelet aggregation. For example, in the treatment of a thrombotic disorder, an agent (i.e., the present disintegrin variant) which decrease, prevents, delays or suppresses or arrests any symptoms of the thrombotic disorder would be effective. An effective amount of an agent is not required to cure a disease or condition but will provide a treatment for a disease or condition such that the onset of the disease or condition is delayed, hindered or prevented, or the disease or condition symptoms are ameliorated. The specific effective or sufficient amount will vary with such factors as the particular condition being treated, the physical condition of the patient (e.g., the patients body mass, age, or gender), the type of mammal or animal being treated, the duration of the treatment, the nature of concurrent therapy (if any), and the specific formulations employed and the like. Effective amount may be expressed, for example, as the total mass of the active agent (e.g., in grams, milligrams or micrograms) or a ratio of mass of the active agent to body mass, e.g., as milligrams per kilogram (mg/kg). The effective amount may be divided into one, two or more doses in a suitable form to be administered at one, two or more times throughout a designated time period.

The term "subject" or "patient" is used interchangeably herein and is intended to mean a mammal including the human species that is treatable by the compound of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In a preferred embodiment, the subject is a human.

The term "pharmaceutically acceptable" refers to molecules and compositions that do not produce an adverse or undesirable reaction (e.g., toxicity, or allergic reaction) when administered to a subject, such as a human.

The term "excipient" and "carrier" are interchangeably used herein to mean any inert substance (such as a powder or liquid) that forms a vehicle/carrier for the active agent. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context dearly dictates otherwise.

2. Detail Description of Preferred Embodiments 2.1 Disintegrin Variants

The present disclosure is based, at least in part, on the unexpected discovery that disintegrin variants derived from TMV-7 or Rho may suppress or inhibit platelet aggregation without affecting the physiological hemostasis. Accordingly, the present disintegrin variants are potential candidates for the development of a medicament for treating diseases, disorders and/or conditions resulting from platelet aggregation.

The practices of this invention are hereinafter described in detail with respect to disintegrin variants, a pharmaceutical composition comprising the same, the preparation of a medicament for preventing or treating thrombosis, or disease caused thereby, in a subject or patient. Results of the present studies, as described herein below, show that the present disintegrin variants may suppress the aggregation or activation of platelets, and thrombus formation in vivo without affecting the bleeding time.

The first aspect of the present application is therefore directed to variants of disintegrin isolated from snake venom, such as rhodostomin (Rho) and trimucrin (TMV-7) that respectively target integrin αIIbβ3. The ability of the present disintegrin variants to bind integrin αIIbβ3 is enabled by mutating at least one amino acid residue in one or more of the linker region, the RGD loop, and the C-terminus of the disintegrin.

Accordingly, the disintegrin variant of the present disclosure comprises in its structure, at least one mutant RGD loop derived from TMV-7 or Rho. For example, the disintegrin variant of the present disclosure may comprise a mutant RGD loop, in which at least one amino acid in the naturally occurring RGD motif, such as the RGD motif of TMV-7 ($^{50}$ARGDNP, SEQ ID No: 2) and the RGD motif of Rho ($^{48}$PRGDMP, SEQ ID No: 5), is substituted and/or deleted. Examples of such variants include, but are not limited to, those having the mutant RGD loop described herein, which has the amino acid sequence selected from the group consisting of SEQ ID Nos. 10, 11, 12, 13, 14, 15, 16, 17, 18, 19, 20, 24 and 25.

Additionally or optionally, the disintegrin variant of the present disclosure may further comprise at least one of a mutant linker and a mutant C-terminus of the disintegrin. For example, the disintegrin variant may comprise a mutant linker, in addition to the mutant RGD loop described above, in which at least one amino acid residue in the naturally occurring linker region, such as the linker region of TMV-7 ($^{41}$KKKRT, SEQ ID No: 1) and the linker region of Rho ($^{39}$SRAGK, SEQ ID No: 4), is to substituted and/or deleted. Examples of such variants include, but are not limited to those having a mutant RGD loop described above, and a mutant linker having the amino acid sequence selected from the group consisting of SEQ ID Nos: 7, 8, and 9.

In other examples, the disintegrin variant further comprises a mutant C-terminus in addition to the mutant RGD loop described above, in which at least one amino acid residue in the naturally occurring C-terminus, such as the C-terminus of TMV-7 ($^{67}$PRNGLYG, SEQ ID No: 3) and the C-terminus of Rho ($^{65}$PRYH, SEQ ID No: 6), is substituted and/or deleted. Examples of such variants include, but are not limited to those having a mutant RGD loop described above, and a mutant C-terminus having the amino acid sequence selected from the group consisting of SEQ ID Nos: 21, 22 and 23.

Further, in any of the variants described above, it may comprise a naturally occurring linker region (i.e., SEQ ID Nos: 1 or 4), and/or a naturally occurring C-terminus (i.e., SEQ ID Nos: 3 or 6) of the disintegrin of interest, in addition to the mutant RGD loop.

According to some embodiments, the present disintegrin variant comprises in its structure, the mutant linker of SEQ ID No: 7; the mutant RGD loop of SEQ ID Nos: 13 or 18; and the C-terminus of SEQ ID Nos: 3, 21 or 22.

According to further embodiments, the present disintegrin variant comprises in its structure, the mutant linker of SEQ ID No: 8; the mutant RGD loop of SEQ ID No: 14; and the mutant C-terminus of SEQ ID No: 21.

According to further embodiments, the present disintegrin variant comprises in its structure, the mutant linker of SEQ ID No: 9; the mutant RGD loop of SEQ ID Nos: 14 or 20; and the C-terminus of any of SEQ ID Nos: 3, 21 or 22.

According to further embodiments, the present disintegrin variant comprises in its structure, the mutant linker of SEQ ID No: 4; the mutant RGD loop of SEQ ID No: 24 or 25; and the C-terminus of SEQ ID No: 6

According to preferred embodiments, the present disintegrin variant comprises in its structure, a naturally occurring linker of SEQ ID NO: 1, a mutant RGD loop having the amino acid sequence of SEQ ID Nos: 10 to 20, and a mutant C-terminus of SEQ ID Nos: 21, 22 or 23. Alternatively, the disintegrin variant in these embodiments comprises in its structure, a naturally occurring linker of SEQ ID NO: 1, a mutant RGD loop having the amino acid sequence of SEQ ID Nos: 10 to 20, and a naturally occurring C-terminus of SEQ ID No: 3. Preferably, the disintegrin variant comprises in its structure, a naturally occurring linker of SEQ ID NO: 1, a mutant RGD loop having the amino acid sequence of SEQ ID No: 14, and a mutant C-terminus of SEQ ID No: 21.

According to other embodiments, the present disintegrin variant comprises in its structure, a naturally occurring linker of SEQ ID NO: 4, a mutant RGD loop having the amino acid sequence of SEQ ID No: 24 or 25, and a naturally occurring C-terminus of SEQ ID No: 6.

The disintegrin variants of the present disclosure may be produced by any method known in the related art. For example, it may be constructed by site-directed mutagenesis. Alternatively, it may be produced by any cloning and expression techniques known in the art, such as by introducing a nucleic acid construct into a host cell (e.g., E. Coli) and cultured the host cell at condition suitable for expression, then harvested the expressed protein either directly from the cultured medium or from the host cell. The present disintegrin variant may be encoded by a modified disintegrin nucleic acid that encodes a modified disintegrin having at least one amino acid residues being substituted and/or deleted from the nature sequence. The coding sequence of a disintegrin variant may be obtained by modifying the coding sequence of a disintegrin of interest from snake venom. Examples of disintegrin suitable for use in the present disclosure include, but are not limited to, albolabrin, applagin, basilicin, batroxostatin, bitistatin, cereberin, cerastin, crotatroxin, durissin, elegantin, eristicophin, flavoridin, flavostatin, halysin, halystatin, jararacin, jarastatin, kistrin, lachesin, lutosin, molossin, rhodostomin, salmosin, saxatilin, tergeminin, trimestatin, trimucrin, trimutase, ussuristatin, and viridian. In some preferred embodiments, the present disintegrin variant are trimucrin (TMV-7) variants. In other embodiments, the present disintegrin variant are rhodostomin (Rho) variants.

Alternatively, the disintegrin variant may be chemically synthesized using techniques known in the art, such as by use of a peptide synthesizer or by solid-state synthesis.

The disintegrin variant of the present disclosure may be recovered or purified from recombinant cell culture by methods such as ammonium sulfate or ethanol precipitation, acid extraction, anion or cation exchange chromatography, affinity chromatography, lectin chromatography and etc. In some embodiments, the high performance liquid chromatography (HPLC) is employed for purification.

The disintegrin variant may be further modified by coupling to a hydrophilic polymer to increase solubility or circulation half-life. Examples of hydrophilic polymer suitable for coupling to the present disintegrin include, but are not limited to, polyalkyl ethers such as polyethylene glycol, polypropylene glycol, polylactic acid, polyglycolic acid, and polyvinyl alcohol; cellulose and its derivatives such as dextran and its derivatives. Preferably, the present disintegrin variant further comprise a polyethylene glycol (PEG)

chain having 2-20 repeats of ethylene glycol (EG) units linked to the N-terminus of the disintegrin variant.

2.2 Pharmaceutical Composition

Another aspect of the present disclosure relates to pharmaceutical composition comprising an effective amount of any disintegrin variant described above, and a pharmaceutically acceptable carrier.

Generally, the present disintegrin variant is present in the pharmaceutical composition at a level of about 0.01% to 99.9% by weight, based on the total weight of the pharmaceutical composition. In some embodiments, the present disintegrin variant is present at a level of at least 0.1% by weight, based on the total weight of the pharmaceutical composition. In certain embodiments, the present disintegrin variant is present at a level of at least 5% by weight, based on the total weight of the pharmaceutical composition. In still other embodiments, the present disintegrin variant is present at a level of at least 10% by weight, based on the total weight of the pharmaceutical composition. In still yet other embodiments, the present disintegrin variant is present at a level of at least 25% by weight, based on the total weight of the pharmaceutical composition.

In some embodiments, the pharmaceutical composition of this invention further includes an agent (e.g., anti-coagulant) known to alleviate or ameliorate the symptoms of the disease, disorder, and/or condition resulting from platelet aggregation. Examples of such agent include, and are not limited to, glycoprotein IIb/IIIa antagonists, heparins, tissue plasminogen activators, Factor Xa inhibitors, thrombin inhibitors, phosphodiesteras inhibitors, cyclooxygenase inhibitors, and etc. Suitable examples of anti-coagulant that may be used in the present method include, and are not limited to, abciximab, apixaban, aspirin, clopidogrel, dipyridamole, edoxaban, eptifibatide, rivaroxaban, tirofiban, ticlopidine, warfarin, and vitamin K.

Pharmaceutically acceptable excipients or carriers are those that are compatible with other ingredients in the formulation and biologically acceptable.

The pharmaceutical composition may comprise different types of excipients or carriers depending on the intended routes of administration. The present composition may be administered intravenously, intradermally, intraarterially, intraperitoneally, intralesionally, intracranially, intranasally, intrapleurally, intratracheally, intrarectally, topically, intramuscularly, subcutaneously, intravesicularily, intrapericardially, intraocularally, orally, topically, locally, injection, inhalation, infusion, localized perfusion, in any suitable forms such as powders, creams, liquids, aerosols and etc.

The actual dosage of the medicament or the pharmaceutical composition may be determined by the attending physician based on the physical and physiological factors of the subject, these factors include, but are not limited to, age, gender, body weight, the disease to be treated, severity of the condition, previous history, the presence of other medications, the route of administration and etc. According to non-limiting examples of the present disclosure, each dosage will give rise to 0.01-100 mg the present disintegrin variant/Kg body weight per administration. Preferably, each dosage will give rise to 0.1-50 mg the present disintegrin variant/Kg body weight per administration The pharmaceutical compositions containing the present disintegrin variant may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the present disintegrin variant in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

For example, a solid oral composition such as a tablet or capsule may contain from 1 to 99% (w/w) the present disintegrin variant; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

When the present disintegrin variant is formulated to be administered by intravenous, cutaneous or subcutaneous injection, the polypeptide will be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition for intravenous, cutaneous, or subcutaneous injection should contain, in addition to the present disintegrin variant, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the invention may also contain stabilizers, preservatives, buffers, antioxidants, or other additives known to those of skill in the art. The duration of intravenous therapy using the pharmaceutical composition of the invention will vary, depending on the severity of the disease being treated and the condition and potential idiosyncratic response of each individual subject. It is contemplated that the duration of each application of the present disintegrin variant will be in the range of 12 to 24 hours of continuous intravenous administration. Ultimately the attending physician will decide on the appropriate duration of intravenous therapy A parenteral formulation may contain from 1 to 50% (w/w) the present disintegrin variant; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilizers, tonicity adjusting agents and preservatives.

The present disintegrin variant may also be formulated into physiologically acceptable form suitable for topically, systematically, or locally administration. For example, the present disintegrin may be applied on the surface of an implant or device. Further, the composition may desirably be encapsulated or injected in a viscous form for delivery to the site tissue damage. Additional useful agents may also optionally be included in the composition, as described above, or may be administered simultaneously or sequentially with the pharmaceutical composition of the invention.

The present disintegrin variant may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the present disintegrin variant are employed. (For purposes of this application, topical application shall include mouth washes and gargles.) Topical formulations may generally be comprised of a pharmaceutical carrier, co-solvent, emulsifier, penetration enhancer, preservative system, and emollient.

2.3 Method of Use

The present invention also aims at providing a method of treating a subject having or suffering from a disease, disorder and/or condition resulted from platelet aggregation. The method comprises administering to the subject in need thereof, the pharmaceutical composition described above, which contains an effective amount of the present disintegrin variant, so as to alleviate or ameliorate the symptoms associated with the disease, disorder and/or condition resulted from platelet aggregation.

In some embodiments, the present disintegrin variant may inhibit the activation of integrin $\alpha IIb\beta 3$, thereby suppressing platelet aggregation. Activation of integrin $\alpha IIb\beta 3$ results in the aggregation of platelets, particularly in subjects suffering from acute vascular disease, which includes but is not limited to, atherothrombosis, deep vein thrombosis, myocardial infarction, pulmonary embolism, peripheral arterial occlusion, stroke, unstable angina and other blood system thromboses.

In other embodiments, the present pharmaceutical composition may prevent or inhibit undesired platelet aggregation in certain medical procedures, such as preventing platelets from aggregating following vascular surgery (e.g., angioplasty or stent placement).

According to some embodiments of the present disclosure, the present pharmaceutical composition is administered to the subject intravenously, subcutaneously, or orally to give rise to the present disintegrin variant in the amount of 0.01-100 mg/Kg, preferably in the amount of 0.1-50 mg/Kg.

According to other embodiments, the present pharmaceutical composition, which comprises the present disintegrin variant is coated on the surface of an implantable device (e.g., a stent or a tube), which is then inserted into blood vessels, urinary tracts or other difficult to access places for the purpose of preventing restenosis, providing vessel or lumen wall support or reinforcement. In this regard, the present pharmaceutical composition is preferably in the form of a solution or a suspension with the present disintegrin variant homogeneously dispersed therein. The coating is preferably applied as a plurality of relatively thin layers sequentially applied in relatively rapid sequence and is preferably applied with the stent in a radially expanded state. The coating may be applied by dipping or spraying using evaporative solvent materials of relatively high vapor pressure to produce the desired viscosity and quickly establish coating layer thicknesses. The coating process enables the present disintegrin variant to adherently conform to and cover the entire surface of the open structure of the stent or the catheter.

According to optional embodiments, the present disintegrin variant may be used in conjugation with another anti-coagulant to treat diseases, disorders, and/or conditions resulted from the activation or aggregation of platelets. Anti-coagulant or platelet inhibitors suitable for use with the present disintegrin variant are, for example, glycoprotein IIb/IIIa antagonists, heparins, tissue plasminogen activators, Factor Xa inhibitors, thrombin inhibitors, phosphodiesteras inhibitors, cyclooxygenase inhibitors, and etc. Suitable examples of anti-coagulant that may be used in the present method include, and are not limited to, abciximab, apixaban, aspirin, clopidogrel, dipyridamole, edoxaban, eptifibatide, rivaroxaban, tirofiban, ticlopidine, warfarin, and vitamin K.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

EXAMPLES

Materials and Methods

Expression and Purification of Disintegrin and its Variants

The expression of disintegrin (i.e., trimucrin (TMV-7) and rhodostomin) and its variants in *P. pastoris* was accomplished by following protocols previously described (Guo et al., Proteins. 2001 43(4), 499-508; Shiu et al., Plos One. 2012 7(1):e28833).

The expression kit and the yeast transfer vector, pPICZαA, were purchased from Invitrogen. The wild-type construct was used to produce the mutations using overlap extension PCR. The construct was transformed into the Pichia strain, X33, using a Pichia EasyComp kit from Invitrogen.

Trimucrin, rhodostomin and their variants were produced by following protocols previously described (Guo et al., Proteins. 2001 43(4), 499-508; Shiu et al., Plos One. 2012 7(1):e28833). Recombinant proteins were produced as follows: 100 µL of cell stock grew at 30° C. in 100 mL of yeast nitrogen base (YNB) medium (1% yeast extract, 2% peptone, and 2% dextrose) containing 100 µg/mL of Zeocin for 48 h. Cells were then transferred into 900 mL of YNB medium. After another 48 h, the cells were collected by centrifugation and grown in 1 L of minimal methanol medium (1.34% YNB with ammonium sulphate without amino acids and $4\times10^{-5}$% biotin). Methanol (1% w/v) was added once every 12 h to induce protein expression for 2 days.

The supernatant was collected by centrifugation and dialyzed twice against 10 L of $H_2O$ and once against 5 L of binding buffer (50 mM Tris-HCl buffer at pH 8.0). The dialyzed solution was loaded into a CaptoMMC column and proteins were eluted using elution buffer containing 500 mM of NaCl. Proteins were then purified using C18 reversed-phase HPLC with a gradient of 20-30% acetonitrile. The recombinant proteins were more than 95% pure, as determined using tricine-SDS-PAGE.

Cell Adhesion Assay

A cell adhesion assay was used to determine the inhibitory activity of Rho, TMV, and their variants and was conducted according to previously described protocols. 96-well microtiter plates (Costar; Corning) were coated with 100 μL PBS buffer containing 200 μg/mL fibrinogen or 50 μg/mL fibronectin, and incubated overnight at 4° C. Non-specific protein binding sites were blocked by incubating each well with 200 μL of heat-denatured 1% bovine serum albumin (BSA) (Calbiochem) at room temperature for 1.5 h. The heat-denatured BSA was discarded and each well was washed twice with 200 μL PBS.

Chinese hamster ovary (CHO) cells that expressed integrins αvβ3 (CHO-αvβ3) and αIIbβ3 (CHO-αIIbβ3) were kindly provided by Dr. Y. Takada (Scripps Research Institute) and maintained in Dulbecco's modified Eagle's medium (18, 27). Human erythroleukemia K562 cell was purchased from ATCC and cultured in Roswell Park Memorial Institute (RPMI)—1640 medium containing 10% fetal bovine serum (FBS). Harvested K562 cells were resuspended in RPMI-1640 medium containing 5% FBS. CHO and K562 cells were diluted to $3\times10^5$ and $2.5\times10^5$ cells/mL, respectively, and 100 μL of the cells were used for the assay.

The adhesions of CHO-αIIbβ3 cells to fibrinogen, CHO-αvβ3 cells to fibrinogen, and K562 cells to fibronectin were used to determine the inhibitory activities of tested protein to integrins αIIbβ3, αvβ3, and α5β1. Rho mutants (0.001-500 μM), which were used as inhibitors, were added to the cells and incubated at 37° C. in a 5% $CO_2$ atmosphere for 15 min. The treated cells were then added to the coated plate and reacted at 37° C. (5% $CO_2$) for 1 h. The reacting solution was then discarded and non-adhered cells were removed by washing them twice with 200 μL PBS. The well was fixed with 100 μL of 10% formalin for 10 min and then dried. A solution of 50 μL of 0.05% crystal violet was added to the well at room temperature for 20 min. Each well was then washed four times with 200 μL distilled water and dried. Colorizing solution (150 μL of 50% alcohol and 0.1% acetic acid) was then added. The resulting absorbance was read at 600 nm and the readings were correlated with the number of adhering cells. Inhibition was defined using the following formula: % inhibition=100−[$OD_{600}$ (Rho and TMV protein-treated sample)/$OD_{600}$ (untreated sample)]×100. The reported half maximal inhibitory calculation ($IC_{50}$) values represent the averages of at least three separate experiments.

Preparation of Human Platelet Suspension (PS)

Blood was collected from healthy volunteers who had not taken any medication for two weeks prior to the study. Informed consents were obtained from each and every participants, and the study was approved by the institutional review board of National Taiwan University Hospital. Preparation of human PS was performed in accordance with procedures described previously (Huang et al., Experimental haemtology. 2008 36(12), 1704-1713).

Safety Index Calculation

The "Safety Index" is defined as the ratio between the concentration of disintegrin in inducing platelet activation in the presence of AP2, an inhibitory mAb raised against αIIbβ3, and $IC_{50}$ on collagen-induced platelet aggregation.

Safety Index=the lowest concentration of disintegrin to activate platelet (combining with 4 μg/ml AP2)/$IC_{50}$ of disintegrin on collagen-induced platelet aggregation.

Animals

Male ICR mice weighing 20-30 g were used in all studies. Animals were allowed to access food and water ad libitum under controlled temperature (20±1° C.) and humidity (55%±5%). The animal experimental protocols were approved by the Laboratory Animal Use Committee of College of Medicine, National Taiwan University.

$FeC_3$-Induced Arterial Thrombosis Model

Male ICR mice were anesthetized with sodium pentobarbital (50 mg/kg) by intra-peritoneal injection, and then an incision was made with a scalpel directly over the right common carotid artery, and a 2-mm section of the carotid artery was exposed. A miniature Doppler flow probe was placed around the artery to monitor blood flow. Mice were intravenously administered with RR (0.125 or 0.25 mg/kg). After 5 min, $FeCl_3$ injury was induced by a filter paper saturated with ferric chloride solution (7.5%). After 3 min exposure, the filter paper was removed and carotid blood flow was monitored continuously until thromboembolism formation or for 80 min.

Tail Bleeding Time

Male ICR mice were intravenously injected through a lateral tail vein of the mouse with agents. A sharp cut of 2 mm segment from the distal tail was made 5 min after injection. The amputated tail was immediately placed into a tube filled with isotonic saline at 37° C. Bleeding time was recorded for a maximum of 10 min and the end point was the arrest of bleeding.

Statistical Analysis

Results were expressed as mean±SEM. Statistical analysis was performed by one-way analysis of variance (ANOVA) and the Newman-Keuls multiple comparison test. P value less than 0.05 (P<0.05) was considered as significant difference.

Example 1 Cloning and Isolation of Disintegrin and its Variants

In this example, trimucrin and rhodostomin, as well as respective mutants thereof, were cloned and isolated in accordance with procedures described in the "Material and Methods" section. Each mutants contained at least one mutated amino acid residues in the linker region, RGD region or C-terminus of the nature protein (i.e., trimucrin (TMV-7) or rhodostomin). The mutated sequences of each variants are summarized in Tables I and 2.

TABLE 1

Respective amino acid sequences of trimucrin and its mutants in the linker, RGD and C-terminus regions

| | Amino acid sequences (SEQ ID No) | | |
|---|---|---|---|
| Name | Linker region | RGD region | C-terminus |
| TMV-7 | $^{41}$KKKRT (SEQ ID No. 1) | $^{50}$ARGDNP (SEQ ID No. 2) | $^{67}$PRNGLYG (SEQ ID No. 3) |
| T/KH | $^{41}$KKKRT (SEQ ID No. 1) | $^{50}$AKGDHP (SEQ ID No. 10) | $^{67}$PRNGLYG (SEQ ID No. 3) |

TABLE 1-continued

Respective amino acid sequences of trimucrin and its mutants in the linker, RGD and C-terminus regions

| Name | Linker region | RGD region | C-terminus |
|---|---|---|---|
| T/KHR | $^{41}$KKKRT (SEQ ID No. 1) | $^{50}$AKGDHP (SEQ ID No. 10) | $^{67}$PRNRLYG (SEQ ID No. 21) |
| T/KY | $^{41}$KKKRT (SEQ ID No. 1) | $^{50}$AKGDYP (SEQ ID No. 11) | $^{67}$PRNGLYG (SEQ ID No. 3) |
| T/KYR | $^{41}$KKKRT (SEQ ID No. 1) | $^{50}$AKGDYP (SEQ ID No. 11) | $^{67}$PRNRLYG (SEQ ID No. 21) |
| T/KWR | $^{41}$KKKRT (SEQ ID No. 1) | $^{50}$AKGDWP (SEQ ID No. 12) | $^{67}$PRNRLYG (SEQ ID No. 21) |
| T/KRR | $^{41}$KKKRT (SEQ ID No. 1) | $^{50}$AKGDRP (SEQ ID No. 13) | $^{67}$PRNRLYG (SEQ ID No. 21) |
| T/KRRR | $^{41}$KKKRT (SEQ ID No. 1) | $^{50}$AKGDRR (SEQ ID No. 14) | $^{67}$PRNRLYG (SEQ ID No. 21) |
| T/KRKR | $^{41}$KKKRT (SEQ ID No. 1) | $^{50}$AKGDRK (SEQ ID No. 15) | $^{67}$PRNRLYG (SEQ ID No. 21) |
| T/KKRR | $^{41}$KKKRT (SEQ ID No. 1) | $^{50}$AKGDKR (SEQ ID No. 16) | $^{67}$PRNRLYG (SEQ ID No. 21) |
| T/KKKR | $^{41}$KKKRT (SEQ ID No. 1) | $^{50}$AKGDKK (SEQ ID No. 17) | $^{67}$PRNRLYG (SEQ ID No. 21) |
| T/IEEGKRR | $^{41}$IEEGT (SEQ ID No. 7) | $^{50}$AKGDRP (SEQ ID No. 13) | $^{67}$PRNRLYG (SEQ ID No. 21) |
| T/AKRRR | $^{41}$KKART (SEQ ID No. 8) | $^{50}$AKGDRR (SEQ ID No. 14) | $^{67}$PRNRLYG (SEQ ID No. 21) |
| T/MGKRRR | $^{41}$MKKGT (SEQ ID No. 9) | $^{50}$AKGDRR (SEQ ID No. 14) | $^{67}$PRNRLYG (SEQ ID No. 21) |
| T/K | $^{41}$KKKRT (SEQ ID No. 1) | $^{50}$AKGDNP (SEQ ID No. 18) | $^{67}$PRNGLYG (SEQ ID No. 3) |
| T/IEEGK | $^{41}$IEEGT (SEQ ID No. 7) | $^{50}$AKGDNP (SEQ ID No. 18) | $^{67}$PRNGLYG (SEQ ID No. 3) |
| T/KS | $^{41}$KKKRT (SEQ ID No. 1) | $^{50}$AKGDNP (SEQ ID No. 18) | $^{67}$PRNS (SEQ ID No. 22) |
| T/IEEGKS | $^{41}$IEEGT (SEQ ID No. 7) | $^{50}$AKGDNP (SEQ ID No. 18) | $^{67}$PRNS (SEQ ID No. 22) |
| T/KR | $^{41}$KKKRT (SEQ ID No. 1) | $^{50}$AKGDRP (SEQ ID No. 13) | $^{67}$PRNGLYG (SEQ ID No. 3) |
| T/KRRFH | $^{41}$KKKRT (SEQ ID No. 1) | $^{50}$AKGDRP (SEQ ID No. 13) | $^{67}$PRNRFH (SEQ ID No. 23) |
| T/KF | $^{41}$KKKRT (SEQ ID No. 1) | $^{50}$AKGDFP (SEQ ID No. 19) | $^{67}$PRNGLYG (SEQ ID No. 3) |
| T/KFRFH | $^{41}$KKKRT (SEQ ID No. 1) | $^{50}$AKGDFP (SEQ ID No. 19) | $^{67}$PRNRFH (SEQ ID No. 23) |
| T/KWN | $^{41}$KKKRT (SEQ ID No. 1) | $^{50}$AKGDWN (SEQ ID No. 20) | $^{67}$PRNGLYG (SEQ ID No. 3) |
| T/KWNR | $^{41}$KKKRT (SEQ ID No. 1) | $^{50}$AKGDWN (SEQ ID No. 20) | $^{67}$PRNRLYG (SEQ ID No. 21) |
| T/KWNRFH | $^{41}$KKKRT (SEQ ID No. 1) | $^{50}$AKGDWN (SEQ ID No. 20) | $^{67}$PRNRFH (SEQ ID No. 23) |

TABLE 1-continued

Respective amino acid sequences of trimucrin and its mutants in the linker, RGD and C-terminus regions

| Name | Linker region | RGD region | C-terminus |
|---|---|---|---|
| | Amino acid sequences (SEQ ID No) | | |
| T/MGTKWNRFH | $^{41}$MKKGT (SEQ ID No. 9) | $^{50}$AKGDWN (SEQ ID No. 20) | $^{67}$PRNRFH (SEQ ID No. 23) |
| T/MGTKWN | $^{41}$MKKGT (SEQ ID No. 9) | $^{50}$AKGDWN (SEQ ID No. 20) | $^{67}$PRNGLYG (SEQ ID No. 3) |

The bold letter indicates the amino acid residue that is mutated or differed from the corresponding amino acid residue of the nature trimucrin.

TABLE 2

Respective amino acid sequences of rhodostomin and its mutants in the linker, RGD and C-terminus regions

| Name | Linker region | RGD region | C-terminus |
|---|---|---|---|
| | Amino acid sequences (SEQ ID No) | | |
| Rhodostomin | $^{39}$SRAGK (SEQ ID No. 4) | $^{46}$PRGDMP (SEQ ID No. 5) | $^{65}$PRYH (SEQ ID No. 6) |
| R/K | $^{41}$SRAGK (SEQ ID No. 4) | $^{46}$PKGDMP (SEQ ID No. 24) | $^{65}$PRYH (SEQ ID No. 6) |
| R/AWN | $^{41}$SRAGK (SEQ ID No. 4) | ARGDWN (SEQ ID No. 25) | $^{65}$PRYH (SEQ ID No. 6) |

The bold letter indicates the amino acid residue that is mutated or differed from the corresponding amino acid residue of the nature rhodostomin.

Example 2 Inhibition of Platelet Aggregation by Disintegrin and/or its Variants of Example 1

Disintegrin and its variants of Example 1 were subject to test for their abilities in suppressing platelet aggregation mediated by αIIbβ3. Briefly, venous blood samples from healthy donors were collected and platelet-rich plasma was prepared therefrom. The platelet-rich plasma was then incubated with the stimulant (e.g., collagen or AP2) that triggered plug formation, then with the disintegrin and/or its variants of Example 1. Results are summarized in Tables 3.

As the data in Table 3 indicated, trimucrin variants, in which the nature C-terminus sequence ($^{67}$PRNGLYG) was changed to $^{67}$PRNRLYG, and the nature RGD loop sequence ($^{50}$ARGDNP) was changed to $^{50}$AKGDWP (T/KW), $^{50}$AKGDYP (T/KY), $^{50}$AKGDHP (T/KH), and $^{50}$AKGDRP, respectively, an increased in the safety index value in these variants was observed (safety indexes for each variants were 8, 9, 12, and 26, respectively); however, when the RGD loop sequence ($^{50}$ARGDNP) was changed to $^{50}$AKGDRR, the safety index increased dramatically to >1300, suggesting the mutant T/KRRR (i.e., $^{41}$KKKRT-$^{50}$AKGDRR-$^{67}$PRNRLYG) would be a good candidate for subsequent development as an anti-coagulant.

In addition, the data also indicated that, trimucrin variants, in which the nature C-terminus sequence ($^{67}$PRNGLYG) was changed to $^{67}$PRNRLYG, and the nature linker region sequence ($^{41}$KKKRT) was changed to $^{41}$IEEGT (T/IEEGR), decreases in both the safety index and anti-platelet aggregation activity were found, suggesting the linker region need to remain unchanged for its anti-platelet aggregation activities.

TABLE 3

Anti-platelet functions of disintegrin and its variants of example 1

| | Disintegrin scaffold | | | Safety | Platelet aggregation | | | Cell adhesion |
|---|---|---|---|---|---|---|---|---|
| | Linker | | | index | IC$_{50}$ (nM) | | | IC$_{50}$ (nM) |
| Name | region | RGD motif | C-terminus | AP2 | ADP | | Collagen | aIIbβ3 |
| TMV-7 | $^{41}$KKKRT | $^{50}$ARGDNP | $^{67}$PRNGLYG | 18 | 184.0 | | 83.8 | |
| Rhodostomin | $^{39}$SRAGK | $^{46}$PRGDMP | $^{65}$PRYH | 2 | 81.5 ±8.0(15) | 66.8 | ±8.9(11) | 59.5 ±16.7(14) |
| R/K | $^{41}$SRAGK | $^{46}$PKGDMP | $^{65}$PRYH | — | 152.4 ±33.1(3) | — | — | 89.8 ±33.8(4) |
| T/K | $^{41}$KKKRT | $^{50}$AKGDNP | $^{67}$PRNGLYG | 20 | 562.6 ±45.8(3) | 104.9 | — | 27341.5 ±4104.9(3) |
| T/KWR | $^{41}$KKKRT | $^{50}$AKGDWP | $^{67}$PRNRLYG | 8 | 106.4 ±30.7(4) | 26.3 | ±5.76(3) | 290 ±77.4(2) |
| T/KYR | $^{41}$KKKRT | $^{50}$AKGDYP | $^{67}$PRNRLYG | 9 | 117.0 ±15.3(3) | 61.0 | ±4.74(3) | 1464.4 ±656.4(3) |
| T/KHR | $^{41}$KKKRT | $^{50}$AKGDHP | $^{67}$PRNRLYG | 12 | 256.5 ±49.7(2) | 80.1 | — | 5985 ±1165(2) |
| T/KRR | $^{41}$KKKRT | $^{50}$AKGDRP | $^{67}$PRNRLYG | 26 | 213.3 ±38.3(3) | 30.9 | ±3.84(3) | 7328.0 ±1043.6(3) |
| T/KRRR | $^{41}$KKKRT | $^{50}$AKGDRR | $^{67}$PRNRLYG | >1300 | 127.1 ±8.7(3) | 30.6 | ±3.26(3) | 6580 ±1991.2(2) |
| T/KRKR | $^{41}$KKKRT | $^{50}$AKGDRK | $^{67}$PRNRLYG | — | 138.4 ±6.9(2) | — | — | 13925 ±3341.8(2) |
| T/IEEGK | $^{41}$IEEGT | $^{50}$AKGDNP | $^{67}$PRNGLYG | 25 | 1045.6 ±118.2(3) | 217.2 | ±24.9(3) | 97613.0 ±19996.3(3) |
| T/KR | $^{41}$KKKRT | $^{50}$AKGDRP | $^{67}$PRNGLYG | 12 | 140.8 ±31.9(3) | 49.9 | — | 6307.3 ±1297(3) |
| T/KH | $^{41}$KKKRT | $^{50}$AKGDHP | $^{67}$PRNGLYG | 16 | 382.0 ±45.5(2) | 99.3 | ±5.08(3) | 15718 ±7083.2(3) |
| T/KY | $^{41}$KKKRT | $^{50}$AKGDYP | $^{67}$PRNGLYG | 8 | 246.5 ±4.5(2) | 44.9 | — | 3304.3 ±1449(3) |
| T/KF | $^{41}$KKKRT | $^{50}$AKGDFP | $^{67}$PRNGLYG | 7 | 153.9 ±18.9(3) | 68.9 | — | 5547.3 ±2014.4(3) |

TABLE 3-continued

Anti-platelet functions of disintegrin and its variants of example 1

| | Disintegrin scaffold | | | Safety index AP2 | Platelet aggregation IC$_{50}$ (nM) | | | Cell adhesion IC$_{50}$ (nM) a11bβ3 | |
|---|---|---|---|---|---|---|---|---|---|
| Name | Linker region | RGD motif | C-terminus | | ADP | | Collagen | | |
| T/KWN | $^{41}$KKKRT | $^{50}$AKGDWN | $^{67}$PRNGLYG | 4 | 124.7 | ±28.0(3) | 67.7 | — | 1780.3 | ±283.2(3) |
| T/KWNR | $^{41}$KKKRT | $^{50}$AKGDWN | $^{67}$PRNRLYG | 8 | 54.6 | ±2.5(2) | 52.4 | — | >692.4 | (45%) |
| T/KS | $^{41}$KKKRT | $^{50}$AKGDNP | $^{67}$PRNS | 17 | 1083 | ±179.4 | 562.0 | — | 39876.3 | ±4104.9(3) |
| T/KRRFH | $^{41}$KKKRT | $^{50}$AKGDRP | $^{67}$PRNRFH | 15 | 192.3 | ±16.8(2) | 66.9 | — | 5599.3 | ±1146.9(3) |
| T/KFRFH | $^{41}$KKKRT | $^{50}$AKGDFP | $^{67}$PRNRFH | 7 | 120.5 | ±32.3(2) | 63.1 | — | 3185.7 | ±436.7(3) |
| T/KWNRFH | $^{41}$KKKRT | $^{50}$AKGDWN | $^{67}$PRNRFH | 4 | 51.0 | ±7.1(5) | 48.4 | — | 976.7 | ±290.8(3) |
| T/MGKWNRFH | $^{41}$MKKGT | $^{50}$AKGDWN | $^{67}$PRNRFH | 4 | 78.8 | ±16.7(3) | 53.2 | — | 790.2 | ±74.7(2) |
| T/MGKWN | $^{41}$MKKGT | $^{50}$AKGDWN | $^{67}$PRNGLYG | 3 | 78.0 | ±6.6(3) | 48.5 | — | 1721 | ±464.5(3) |
| T/IEEGKS | $^{41}$IEEGT | $^{50}$AKGDNP | $^{67}$PRNS | 35 | 562.6 | ±45.8(3) | 632.4 | — | >195417 | (35%) |
| T/IEEGKRR | $^{41}$IEEGT | $^{50}$AKGDRP | $^{67}$PRNRLYG | 14 | 511.2 | ±104.0(3) | 57.5 | ±9.85(3) | 33805 | ±15192(4) |

The bold letter indicates the amino acid residue that is mutated or differed from the corresponding amino acid residue of the nature protein. "-" stands for not determined.

Figure 1B:
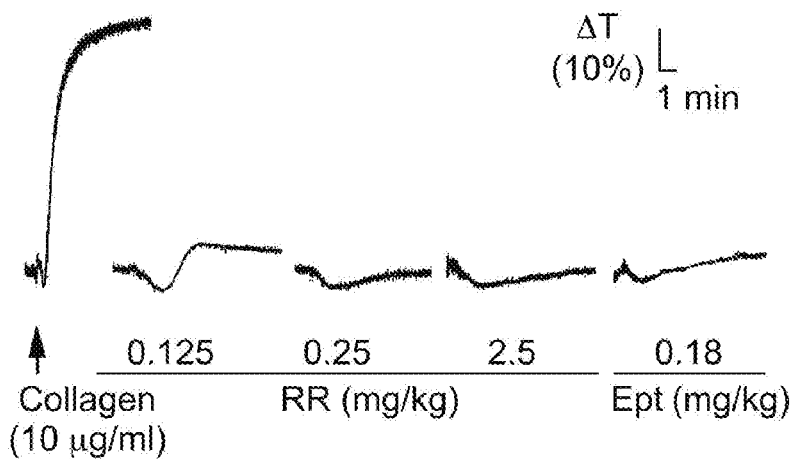
Figure 1C:
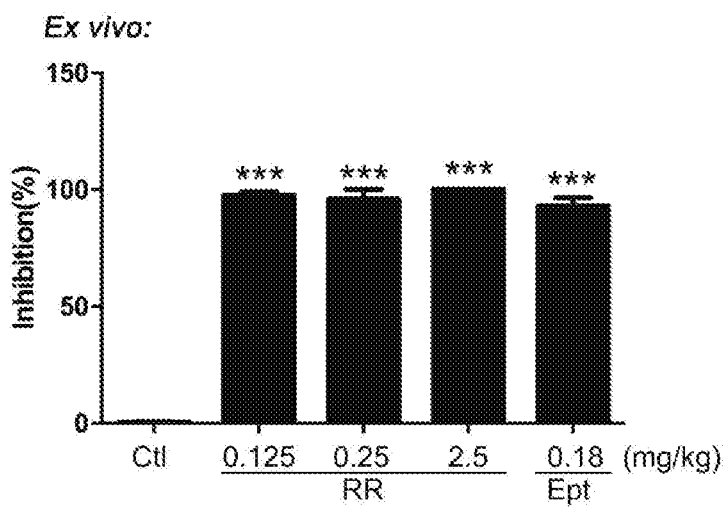
Figure 1E:
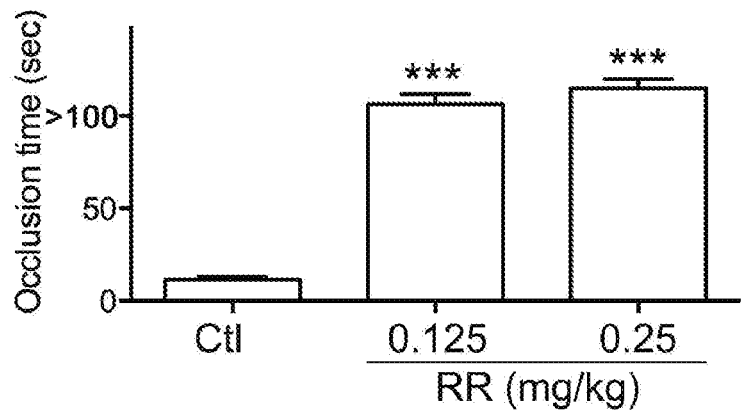
FIGS. 1D and 1E depicts the effect of trimucrin T/KRRR mutant (RR) on inhibiting $FeCl_3$-induced carotid artery thrombosis in accordance with one embodiment of this invention, Typical arterial blood flow charts (D) of $FeCl_3$-induced occlusive thrombosis of mice (E) are shown. (mean±s.e.m, error bars, ***P<0.001 compared with control group by Dunnett's test)
Figure 1F:
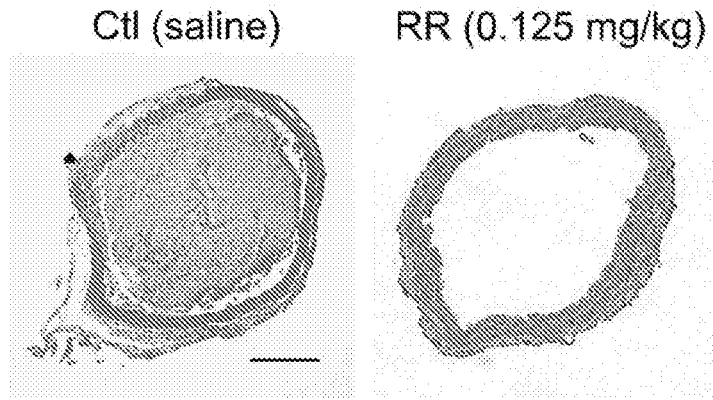
FIG. 1F are photographs of the histologic section of $FeCl_3$-treated carotid artery in accordance with one embodiment of this invention.
Figure 1D:
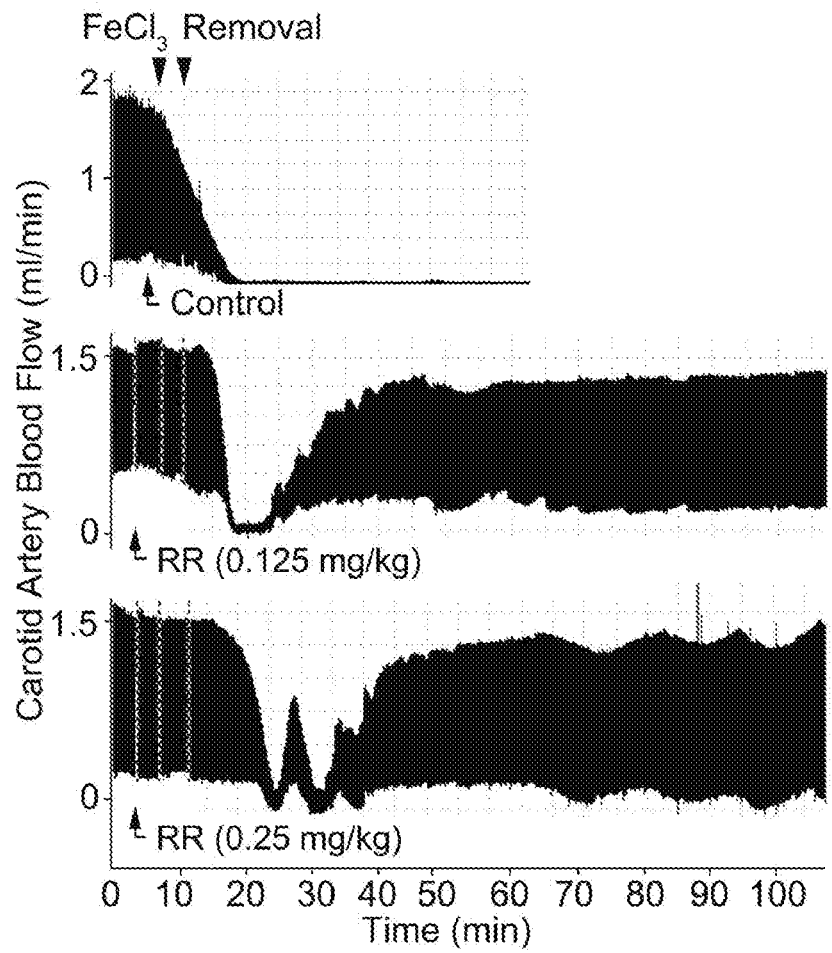
Figure 1G:
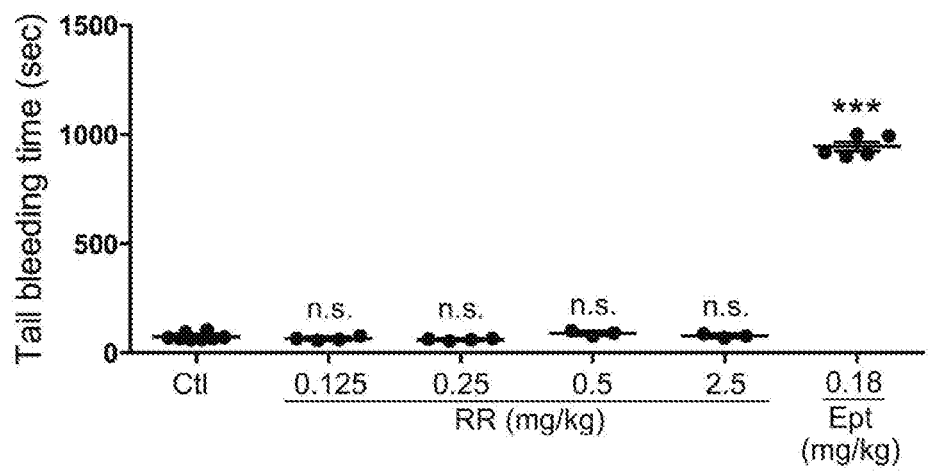
FIG. 1G depicts the effect of rimucrin T/KRRR mutant (RR) or eptfibatide on tail bleeding time of mice in accordance with one embodiment of this invention. Each different symbol represents the bleeding time of the individual mouse. (mean±s.e.m, error bars, ***P<0.001 compared with control group by Dunnett's test; n.s, non-significance).

Example 3 Effect of Trimucrin T/KRRR Mutant and Eptifibatide on Platelet Aggregation and Thrombus Formation The anti-platelet function of trimucrin T/KRRR mutant identified from Example 1 was investigated by measuring the collagen induced aggregation response, the tail bleeding time and the formation of thrombosis in microvessels in the experimental animals. Results are depicted in FIG. 1.

The effect of trimucrin T/KRRR mutant (denoted as RR in FIG. 1) on collagen-induced platelet aggregation was compared with that of another known anti-platelet agent—eptifibatide, a cyclic heptapeptide derived from a protein found in the venom of the southeastern pygmy rattlesnake. The collagen-induce platelet aggregation response was significantly suppressed by T/KRRR mutant, as well as by eptifibatide (FIG. 1, panels B and C), and the suppression was dose-dependent, in which the $IC_{50}$ values of T/KRRR mutant and eptifibatide were 0.25 μg/mL and 0.75 μg/mL, respectively (FIG. 1, panel A).

The effects of T/KRRR mutant on $FeCl_3$-induced thrombus formation were also investigated by the measurement of the occlusion time in the carotid artery. As depicted in FIG. 1, panels D to F, artery occlusion occurred in untreated animals within 10 min after $FeCl_3$ injury. By contrast, T/KRRR mutant (at 0.125 and 0.25 mg/Kg) prevented occlusive thrombosis over 80 min after $FeCl_3$ injury, even recovered the blood flow after thrombus formation. The size of thrombi formed within the vascular lumen of T/KRRR mutant treated animal was much smaller than that found in the untreated animal (FIG. 1, panel F).

In the bleeding test, eptifibatide (0.18 mg/Kg) significantly prolong the bleeding time, however, the T/KRRR mutant administered intravenously at the concentration of 0.125 mg/Kg or even higher concentration (i.e., 2.5 mg/Kg) did not prolong the bleeding time. The results indicated that T/KRRR mutant may effectively suppress the platelet aggregation and thrombus formation, yet it does not affect the bleeding time.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

Example 4 Inhibition of Integrins αIIbβ3, αvβ3, and α5β1

In this example, the respective abilities of Rho, TMV-7, and their mutants in suppressing integrins αIIbβ3, αvβ3, and α5β1 to their ligands were determined. Results are summarized in Table 4.

As the data in Table 4 indicates, Rho and its R/KWN mutant ($^{48}$ARGDWN-$^{65}$PRYH) inhibited the adhesion of CHO cells that expressed integrin αIIbβ3 to immobilized-fibrinogen with $IC_{50}$ values of 52.2±8.2 and 162.8±7.2 nM, respectively. In contrast, Rho and its $^{48}$ARGDWN-$^{65}$PRYH mutant inhibited the adhesion of CHO cells that expressed integrin αvβ3 to immobilized-fibrinogen with $IC_{50}$ values of 13.0±5.7 and 246.6±66.8 nM, respectively. Rho and its R/KWN mutant ($^{48}$ARGDWN-$^{65}$PRYH) inhibited integrin α5β1 adhesion to immobilized-fibronectin with $IC_{50}$ values of 256.8±87.5 and 8732.2±481.8 nM, respectively. Their differences in inhibiting integrins αIIbβ3, αvβ3, and α5β1 were 3.1-, 19.0-, and 34.0-fold. These results indicated that Rho containing a $^{48}$ARGDWN sequence exhibited selectivity for binding with integrin αIIbβ3. Trimucrin mutant—T/KRRR mutant ($^{50}$AKGDRR-$^{67}$PRNRLYG) exhibited low activities in inhibiting cell-expressing integrins αIIbβ3, αvβ3, and α5β1 to their ligands. In contrast, it has high activity in inhibiting platelet aggregation.

TABLE 4

Inhibition of integrins aIIbβ3, avβ3, and a5β1 by Rho, its $^{48}$ARGDWN mutant, and trimucrin T/KRRR mutant

| Proteins | | $IC_{50}$ (nM) | | | Platelet |
|---|---|---|---|---|---|
| Name | Sequence | avβ3 | a5β1 | aIIbβ3 | Aggregation |
| Rho | $^{48}$PRGDMP-$^{65}$PRYH | 13.0 ± 5.7 | 256.8 ± 87.5 | 52.2 ± 8.2 | 83.2 ± 10.4 |
| R/AWN | $^{48}$ARGDWN-$^{65}$PRYH | 246.6 ± 66.8 | 8732.2 ± 481.8 | 162.8 ± 7.2 | 187.8 ± 67.8 |
| T/KRRR | $^{50}$AKGDRR-$^{67}$PRNRLYG | >10000.0 | >10000.0 | 6580.0 ± 1991.2 | 127.1 ± 8.7 |

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A disintegrin variant comprising:
   (a) a linker having the amino acid sequence of SEQ ID No. 1;
   (b) a RGD loop having the amino acid sequence of SEQ ID No. 14; and
   (c) a C-terminus having the amino acid sequence of SEQ ID No. 21.

2. The disintegrin variant of claim 1, wherein the disintegrin is albolabrin, applagin, basilicin, batroxostatin, bitistatin, cereberin, cerastin, crotatroxin, durissin, elegantin, eristicophin, flavoridin, flavostatin, halysin, halystatin, jararacin, jarastatin, kistrin, lachesin, lutosin, molossin, rhodostomin, salmosin, saxatilin, tergeminin, trimestatin, trimucrin, trimutase, ussuristatin, or viridian.

3. The disintegrin variant of claim 1, further comprising a polyethylene glycol (PEG) chain having 2-20 repeats of ethylene glycol (EG) units linked to the N-terminus of the disintegrin variant.

4. A pharmaceutical composition comprising an effective amount of the disintegrin variant of claim 1, and a pharmaceutically acceptable carrier.

5. The pharmaceutical composition of claim 4, wherein the N-terminus of the disintegrin variant further comprises a polyethylene glycol (PEG) chain having 2-20 repeats of ethylene glycol (EG) units linked thereto.

6. A method of treating a subject having or suspected of having a disease resulting from platelet aggregation comprising administering to the subject the pharmaceutical composition of claim 4, for alleviating or ameliorating the symptoms associated with the disease.

7. The method of claim 6, wherein the disease is a thrombotic disorder.

8. The method of claim 7, wherein the thrombotic disorder is selected from the group consisting of, abrupt vessel closure following angioplasty or stent placement, atherothrombosis, acute thrombotic stroke, myocardial infarction, thrombosis resulted from periphery vascular surgery, unstable angina, and venous thrombosis.

9. The method of claim 6, further comprising administering an anti-coagulant to the subject.

10. The method of claim 9, wherein the anti-coagulant is selected from the group consisting of, abciximab, apixaban, aspirin, clopidogrel, dipyridamole, edoxaban, eptifibatide, rivaroxaban, tirofiban, ticlopidine, warfarin, and vitamin K.

11. The method of claim 6, wherein the N-terminus of the disintegrin variant further comprises a polyethylene glycol (PEG) chain having 2-20 repeats of ethylene glycol (EG) units linked thereto.

12. The method of claim 6, wherein the disintegrin variant is applied as a coating on an implantable device.

13. The method of claim 12, wherein the implantable device is a stent or a catheter.

* * * * *

SEQUENCE LISTING

<160> NUMBER OF SEQ ID NOS: 25

<210> SEQ ID NO 1
<211> LENGTH: 5
<212> TYPE: PRT
<213> ORGANISM: Artificial Sequence
<220> FEATURE:
<223> OTHER INFORMATION: TMV-7_Linker region

<400> SEQUENCE: 1

Lys Lys Lys Arg Thr
1               5

<210> SEQ ID NO 2
<211> LENGTH: 6
<212> TYPE: PRT
<213> ORGANISM: Artificial Sequence
<220> FEATURE:
<223> OTHER INFORMATION: TMV-7_RGD region

<400> SEQUENCE: 2

Ala Arg Gly Asp Asn Pro
1               5

<210> SEQ ID NO 3
<211> LENGTH: 7
<212> TYPE: PRT
<213> ORGANISM: Artificial Sequence
<220> FEATURE:
<223> OTHER INFORMATION: TMV-7_C-terminus

<400> SEQUENCE: 3

Pro Arg Asn Gly Leu Tyr Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Rhodostomin_Linker region

<400> SEQUENCE: 4

Ser Arg Ala Gly Lys
1               5

<210> SEQ ID NO 5
<211> LENGTH: 6
<212> TYPE: PRT
<213> ORGANISM: Artificial Sequence
<220> FEATURE:
<223> OTHER INFORMATION: Rhodostomin_RGD region

<400> SEQUENCE: 5

Pro Arg Gly Asp Met Pro
1               5

<210> SEQ ID NO 6
<211> LENGTH: 4
<212> TYPE: PRT
<213> ORGANISM: Artificial Sequence
<220> FEATURE:
<223> OTHER INFORMATION: Rhodostomin_C-terminus

<400> SEQUENCE: 6

Pro Arg Tyr His
1

```
<210> SEQ ID NO 7
<211> LENGTH: 5
<212> TYPE: PRT
<213> ORGANISM: Artificial Sequence
<220> FEATURE:
<223> OTHER INFORMATION: T/IEEGKRR_Linker region

<400> SEQUENCE: 7

Ile Glu Glu Gly Thr
1               5

<210> SEQ ID NO 8
<211> LENGTH: 5
<212> TYPE: PRT
<213> ORGANISM: Artificial Sequence
<220> FEATURE:
<223> OTHER INFORMATION: T/AKRRR_Linker region

<400> SEQUENCE: 8

Lys Lys Ala Arg Thr
1               5

<210> SEQ ID NO 9
<211> LENGTH: 5
<212> TYPE: PRT
<213> ORGANISM: Artificial Sequence
<220> FEATURE:
<223> OTHER INFORMATION: T/MGKRRR_Linker region

<400> SEQUENCE: 9

Met Lys Lys Gly Thr
1               5

<210> SEQ ID NO 10
<211> LENGTH: 6
<212> TYPE: PRT
<213> ORGANISM: Artificial Sequence
<220> FEATURE:
<223> OTHER INFORMATION: T/KH_RGD region

<400> SEQUENCE: 10

Ala Lys Gly Asp His Pro
1               5

<210> SEQ ID NO 11
<211> LENGTH: 6
<212> TYPE: PRT
<213> ORGANISM: Artificial Sequence
<220> FEATURE:
<223> OTHER INFORMATION: T/KY_RGD region

<400> SEQUENCE: 11

Ala Lys Gly Asp Tyr Pro
1               5

<210> SEQ ID NO 12
<211> LENGTH: 6
<212> TYPE: PRT
<213> ORGANISM: Artificial Sequence
<220> FEATURE:
<223> OTHER INFORMATION: T/KWR_RGD region

<400> SEQUENCE: 12

Ala Lys Gly Asp Trp Pro
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: T/KRR_RGD region

<400> SEQUENCE: 13

Ala Lys Gly Asp Arg Pro
1               5

<210> SEQ ID NO 14
<211> LENGTH: 6
<212> TYPE: PRT
<213> ORGANISM: Artificial Sequence
<220> FEATURE:
<223> OTHER INFORMATION: T/KRRR_RGD region

<400> SEQUENCE: 14

Ala Lys Gly Asp Arg Arg
1               5

<210> SEQ ID NO 15
<211> LENGTH: 6
<212> TYPE: PRT
<213> ORGANISM: Artificial Sequence
<220> FEATURE:
<223> OTHER INFORMATION: T/KRKR_RGD region

<400> SEQUENCE: 15

Ala Lys Gly Asp Arg Lys
1               5

<210> SEQ ID NO 16
<211> LENGTH: 6
<212> TYPE: PRT
<213> ORGANISM: Artificial Sequence
<220> FEATURE:
<223> OTHER INFORMATION: T/KKRR_RGD region

<400> SEQUENCE: 16

Ala Lys Gly Asp Lys Arg
1               5

<210> SEQ ID NO 17
<211> LENGTH: 6
<212> TYPE: PRT
<213> ORGANISM: Artificial Sequence
<220> FEATURE:
<223> OTHER INFORMATION: T/KKKR_RGD region

<400> SEQUENCE: 17

Ala Lys Gly Asp Lys Lys
1               5

<210> SEQ ID NO 18
<211> LENGTH: 6
<212> TYPE: PRT
<213> ORGANISM: Artificial Sequence
<220> FEATURE:
<223> OTHER INFORMATION: T/K_RGD region

<400> SEQUENCE: 18

Ala Lys Gly Asp Asn Pro
1               5
```

```
<210> SEQ ID NO 19
<211> LENGTH: 6
<212> TYPE: PRT
<213> ORGANISM: Artificial Sequence
<220> FEATURE:
<223> OTHER INFORMATION: T/KF_RGD region

<400> SEQUENCE: 19

Ala Lys Gly Asp Phe Pro
1               5

<210> SEQ ID NO 20
<211> LENGTH: 6
<212> TYPE: PRT
<213> ORGANISM: Artificial Sequence
<220> FEATURE:
<223> OTHER INFORMATION: T/KWN_RGD region

<400> SEQUENCE: 20

Ala Lys Gly Asp Trp Asn
1               5

<210> SEQ ID NO 21
<211> LENGTH: 7
<212> TYPE: PRT
<213> ORGANISM: Artificial Sequence
<220> FEATURE:
<223> OTHER INFORMATION: T/KHR_C-terminus

<400> SEQUENCE: 21

Pro Arg Asn Arg Leu Tyr Gly
1               5

<210> SEQ ID NO 22
<211> LENGTH: 4
<212> TYPE: PRT
<213> ORGANISM: Artificial Sequence
<220> FEATURE:
<223> OTHER INFORMATION: T/KS_C terminus

<400> SEQUENCE: 22

Pro Arg Asn Ser
1

<210> SEQ ID NO 23
<211> LENGTH: 6
<212> TYPE: PRT
<213> ORGANISM: Artificial Sequence
<220> FEATURE:
<223> OTHER INFORMATION: T/KRRFH_C terminus

<400> SEQUENCE: 23

Pro Arg Asn Arg Phe His
1               5

<210> SEQ ID NO 24
<211> LENGTH: 6
<212> TYPE: PRT
<213> ORGANISM: Artificial Sequence
<220> FEATURE:
<223> OTHER INFORMATION: R/K_RGD region

<400> SEQUENCE: 24

Pro Lys Gly Asp Met Pro
1               5

<210> SEQ ID NO 25
```

```
<211> LENGTH: 6
<212> TYPE: PRT
<213> ORGANISM: Artificial Sequence
<220> FEATURE:
<223> OTHER INFORMATION: R/AWN_RGD region

<400> SEQUENCE: 25

Ala Arg Gly Asp Trp Asn
1               5
```